US006300389B1

(12) United States Patent
Sato et al.

(10) Patent No.: US 6,300,389 B1
(45) Date of Patent: Oct. 9, 2001

(54) DENTAL RESTORATIVE MATERIAL

(75) Inventors: Hisashi Sato; Hideki Yarimizu, both of Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/222,788

(22) Filed: Dec. 30, 1998

(30) Foreign Application Priority Data

Jan. 16, 1998 (JP) ................................................. 10-018333

(51) Int. Cl.$^7$ ...................................................... A61K 6/083
(52) U.S. Cl. ...................... 523/116; 433/228.1; 523/117; 523/118; 524/492; 524/493; 524/444; 524/560; 106/36; 522/81; 522/83; 522/182; 522/183; 522/908
(58) Field of Search ..................................... 523/116, 117, 523/118; 524/492, 560, 444, 493; 106/35; 522/81, 83, 182, 183, 908; 433/228.1

(56) References Cited

U.S. PATENT DOCUMENTS

| | | | |
|---|---|---|---|
| 4,540,723 | * | 9/1985 | Ying . |
| 4,764,497 | * | 8/1988 | Yuasa et al. . |
| 5,063,257 | * | 11/1991 | Akahane et al. ...................... 523/116 |
| 5,154,762 | * | 10/1992 | Mitra et al. ............................ 523/116 |
| 5,171,763 | * | 12/1992 | Ohno et al. . |
| 5,520,725 | * | 5/1996 | Kato et al. . |
| 5,708,051 | * | 1/1998 | Erdrich et al. . |
| 5,846,075 | * | 12/1998 | Suh et al. . |
| 5,871,360 | * | 2/1999 | Kato ...................................... 523/116 |
| 6,126,922 | * | 10/2000 | Rozzi et al. .......................... 523/116 |

OTHER PUBLICATIONS

Grant & Hackh's Chemical Dictionary, McGrawHill Book Company, Fifth Edition, p. 23, 1987.*

* cited by examiner

*Primary Examiner*—Peter Szekely
(74) *Attorney, Agent, or Firm*—Oblon, Spivak, McClelland, Maier & Neustadt, P.C.

(57) ABSTRACT

A dental restorative material is disclosed, comprising an amorphous inorganic material having a refractive index in a D-line of sodium in the range of 1.470~1.520 and having an X-ray opacity; a (meth)acrylic ester monomer not having a benzene ring in a molecule thereof; and a polymerization initiator, if desired, the dental restorative material according to the invention further comprises an amorphous inorganic material having a refractive index in a D-line of sodium equal to or less than that of the (meth)acrylic ester monomer not having a benzene ring in a molecule thereof, the dental restorative material of the invention has an X-ray opacity and translucency close to natural teeth, and has superior esthetics not using a monomer having a benzene ring which has a fear of an environmental hormone action.

10 Claims, No Drawings

US 6,300,389 B1

DENTAL RESTORATIVE MATERIAL

FIELD OF THE INVENTION

The present invention relates to a dental resin material. More particularly, the present invention relates to a dental restorative material which is used as a dental filling restoration material, a rebuilding material of abutment tooth, a sealing material pit and fissure, dental prostheses such as an inlay, a crown, and a bridge, a resin cement, and a denture material.

BACKGROUND OF THE INVENTION

Hitherto, components which are used in order to impart an X-ray opacity to dental restorative materials contain elements having a mass number equal to or higher than that of strontium. Oxides or sulfates of these elements have a high refractive index. In addition, in case of the sulfates, since they are crystalline with low symmetry, when they are used for a dental restorative material as a polycrystalline powder, their transparency is deteriorated. Accordingly, in case where esthetics is required, and translucency close to that in a tooth is to be obtained, their amount for use is restricted.

Also, fluorides of these elements have a refractive index lower than that of the oxides or sulfates (for example, the refractive index of ytterbium trifluoride is 1.53), the modifying effect of generally employed silane coupling agents is low, the mechanical characteristics are hardly realized. Accordingly, their amount for use is restricted.

For these reasons, components which are generally employed at present in order to impart an X-ray opacity are an oxide-glass containing barium, and a glass containing barium in an amount enough to have X-ray opacity (this glass being hereunder referred to as "barium oxide glass") has a refractive index of 1.53 or more. Such a barium oxide glass is combined with α-quartz (refractive index: 1.544 & 1.553) with no X-ray opacity, which had been used prior to the time when importance was attached to the X-ray opacity, and used as a dental restorative material.

Hitherto, as matrix monomers to be used to obtain a dental restorative material having translucency close to that of a tooth by using a such a barium oxide glass and α-quartz, since they are required to have a high refractive index, monomers or oligomers having a benzene ring in a molecular structure thereof, and particularly "bis-phenol A" (hereafter to be referred to as bisphenol A) in a molecule thereof were suitably used. Besides, as monomers for making the viscosity low and having a high refractive index, mono-(meth)acryloyl monomers such as phenyl (meth)acrylate, phenoxyethyl (meth)acrylate, and benzyl (meth)acrylate were used.

In recent years, some of the chemical substances which are generally employed are pointed out to cause an action against living bodies similar to that of hormones (these chemical substances being called as "environmental hormones" or "environmental endocrine disruptors, etc."). Of these substances, there are chemical substances having a benzene ring, and nonyl phenol which is formed upon decomposition of a surfactant or bisphenol A which is generally employed in epoxy resins, etc. are exemplified as a causative substance thereof. Of monomers or oligomers which are generally employed in the dental field, there are ones obtained by modifying bisphenol A with epichlorohydrin, etc. and (meth)acryloyl a terminal end(s) thereof. Since such monomers or oligomers are purified so that the bisphenol A is not substantially eluted out, but a pseudohormonal action takes place in an extremely low concentration, so the elution of the bisphenol A from these monomers or oligomers becomes a problem.

In the light of the above, in these conventional technologies used monomers having a benzene ring, in order to obtain a dental restorative material having an X-ray opacity and having translucency close to that of a tooth, there was a fear of the action as an environmental hormone.

On the other hand, in order to give translucency close to that of a natural tooth to a dental restorative material, the adjusting of a refractive index between a matrix monomer and a filler is carried out.

The inventions as disclosed in Japanese Patent Publication No. 4-48801(1992) and Japanese Patent Publication No. 7-45373(1995) are concerned with a technology in which while paying an attention to the difference in refractive index, a fluctuation of the translucency of a dental restorative material due to the change in refractive index by curing of a matrix monomer is intended to make small. The invention as disclosed in Japanese Patent Laid-Open No. 9-169613(1997) is concerned with a technology in which it is an index for the translucency to define a degree of diffusion from the angle reliance of a transmitted light. However, even components which are satisfied with these requirements are insufficient in esthetics from the clinical standpoint, and a deviation in hue is generated due to the thickness of a dental restorative material. One of the causes is one by light scattering of colloidal silica having a mean particle size of from 20 to 70 nm, in which a so-called opal-effect to be generated by the fact that the visible light in a short wavelength is scattered, while the visible light in a long wavelength is transmitted. This opal-effect is slightly observed on human teeth and hence, it is considered to be necessary to properly impart it to a dental restorative material. However, if a volume fraction of colloidal silica in the dental restorative material is too high, the hue becomes strong in red at the portion of a thin filling layer, while the hue becomes strong in blue, and the lightness is high at the portion of a thin filling layer. That is, the hue relies on the thickness of the filling layer thereof. Even when the colloidal silica is eliminated, there is generated a tendency in which the hue relies on the thickness of the filling layer in compounding in the examples as disclosed in Japanese Patent Publication No. 4-48801(1992) and Japanese Patent Publication No. 7-45373(1995). In other words, when not only the refractive index in a D-line of sodium of an organic material such as the matrix monomer exceeds that of an inorganic material such as colloidal silica, but also the volume fraction of said inorganic materials is large, opal-effect like optical characteristics are realized, and the hue is liable to rely on the thickness of the filling layer. In particular, when the filling layer is thick, the hue becomes bluish, and such fails in the esthetics from the clinical standpoint.

SUMMARY OF THE INVENTION

Thus, an object of the present invention is to overcome the defects of the conventional dental restorative materials and to provide a novel dental restorative material not using a benzene ring-containing monomer which has a fear of an environmental hormone action and having an X-ray opacity and translucency close to that of a tooth.

In order to achieve the above-described object, the present inventors made extensive and intensive investigations. That is, studies were made on amorphous inorganic materials having a refractive index in a D-line of sodium of from 1.470 to 1.520 and having an X-ray opacity, which is capable of realizing translucency close to that of a natural tooth, by using a monomer matrix having no benzene ring. As a result, a dental restorative material which is free from a fear of an environmental hormone action, has an X-ray opacity, has superior translucency as a dental restorative material, and has superior esthetics such that the hue does not rely on the thickness of a filling layer was found leading to accomplishment of the present invention.

That is, the present invention relates to a dental restorative material comprising an amorphous inorganic material having a refractive index in a D-line of sodium in the range of from 1.470 to 1.520 and having an X-ray opacity; a (meth) acrylic ester monomer not having a benzene ring in a molecule thereof; and a polymerization initiator. The dental restorative material according to the present invention may further contain an amorphous inorganic material having a refractive index in a D-line of sodium equal to or less than that of the (meth)acrylic ester monomer not having a benzene ring in a molecule thereof.

DETAILED DESCRIPTION OF THE INVENTION

The dental restorative material according to the present invention is hereunder described in more detail with reference to each of the constitutional components.

As the "amorphous inorganic material having a refractive index in a D-line of sodium in the range of 1.470~1.520 and having an x-ray opacity", which is a first major constitutional component, is used a fluoroaluminosilicate glass. Specifically, "aluminosilicate glasses" as described in Japanese Patent Publication No. 7-55882(1995), "containing, as constitutional components, Si, Al, P, Sr, F, and O, whose conversion amounts are from 20 to 50% by weight for $SiO_2$, from 20 to 40% by weight for $Al_2O_3$, from 0 to 15% by weight for $P_2O_5$, from 15 to 40% by weight for SrO, and from 1 to 20% by weight for $F_2$, respectively and substantially free from alkali metal elements and from Be, Mg, and Ba as alkali earth metal elements". Of these is particularly suitable an aluminosilicate glass with $F_2$ in the range of 3~20% by weight. Also, if desired, the amorphous inorganic material can contain lanthanide metal elements such as La, Gd, and Yb. While the Sr element is an element to contribute to the realization of an X-ray opacity, it has an action to increase the refractive index of oxides-glasses. Accordingly, in case where an oxide-glass containing this element is used for the dental restorative material, a monomer containing a benzene ring is required. However since fluorine has an action to lower the refractive index of oxide-glass, even when Sr element is contained, it is not necessary to use a monomer containing a benzene ring. It is preferred that such an amorphous inorganic material is contained in an amount of from about 25 to 75% by volume in the dental restorative material according to the present invention.

In order to control the opal-effect, if desired, the dental restorative material containing such an amorphous inorganic material may further contain an amorphous inorganic material having a refractive index equal to or less than that of a polymer of "a (meth)acrylic ester monomer not having a benzene ring in a molecule thereof", which is a second major constitutional component as described later. Usually, a suitable content thereof is from 0.01 to 7% by volume. Examples of the amorphous inorganic material having a refractive index equal to or less than that of the polymer of the (meth)acrylic ester monomer not having a benzene ring in a molecule thereof are those containing at least Si and O as constitutional elements. Specific examples include aluminosilicate glasses containing an alkali element and/or an alkaline earth element, aluminoborosilicate glasses containing an alkali element and/or an alkaline earth element, and amorphous silica, in addition to the above-described fluoroaluminosilicate glasses. Glasses having a refractive index equal to or less than that of the polymer of the (meth)acrylic ester monomer not having a benzene ring in a molecule thereof are properly selected and used.

The amorphous inorganic material having a refractive index in a D-line of sodium in the range of from 1.470 to 1.520 and having an X-ray opacity and the amorphous inorganic material having a refractive index equal to or less than that of the polymer of the (meth)acrylic ester monomer not having a benzene ring in a molecule thereof, which is contained, if desired, are adjusted to have a particle size depending on the purpose and used. That is, in case that they are used as a dental restorative material required to have surface smoothness and esthetics in terms of a cured product, it is preferred to use a fine powder having a maximum particle size of 10 μm or less and a mean particle size of 5 μm or less and particularly, a powder having a maximum particle size in the range of 0.05~7 μm and a mean particle size in the range of 0.01~2.0 μm. On the other hand, in case that they are used for rebuilding of abutment tooth or sealing of pit and fissure, those having a larger particle size can also be suitably used, so that a powder having a mean particle size of 50 μm or less can be used. In addition, as the amorphous inorganic material having a refractive index equal to or less than that of the polymer of the (meth)acrylic ester monomer not having a benzene ring in a molecule thereof, which is contained, if desired, in particular, in case that its chemical composition is simple, amorphous silica prepared by a method called as the sol-gel method or spherical amorphous silica prepared by burning and oxidizing a metal is suitably used.

Also, the amorphous inorganic material as a first major constitutional component and the amorphous inorganic material which is used, if desired in combination with the former amorphous inorganic material may be modified on its surface with a silane coupling agent having an unsaturated double bond and compounded into the dental restorative material according to the present invention. Examples of silane coupling agents having an unsaturated double bond which can be used for the modification include 3-methacryloxypropyl trimethoxysilane, 3-methacryloxypropyl triethoxysilane, 3-acryloxypropyl trimethoxysilane, 3-methacryloxypropylmethyl dimethoxysilane, 3-methacryloxypropylmethyl diethoxysilane, 3-acryloxypropylmethyl dimethoxysilane, 2-methacryloxyethoxypropyl trimethoxysilane, vinyl trimethoxysilane, vinyl triethoxysilane, and vinyl tris(2-methoxyethoxy)silane. Besides, silane coupling agents having a glycidoxy group, an amino group, or a mercapto group can be selected depending on the monomer to be composited and mixed with the silane coupling agent having an unsaturated double bond.

Examples of the "(meth)acrylic ester monomer not having a benzene ring in a molecule thereof", which is used as a second major constitutional component, are monomers or resins having an unsaturated double bond, such as unsaturated polyesters. Specific examples include methyl methacrylate, ethyl methacrylate, isopropyl methacrylate, 2-hydroxyethyl methacrylate, 3-hydroxypropyl methacrylate, 2-hydroxy-1,3-dimethacryloxypropane, n-butyl methacrylate, isobutyl methacrylate, hydroxypropyl methacrylate, tetrahydrofurfuryl methacrylate, glycidyl methacrylate, 2-methoxyethyl methacrylate, 2-ethylhexyl methacrylate, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate, and pentaerythritol tetramethacrylate; acrylates corresponding to these methacrylates; and methacrylates or acrylates having a urethane bond in a molecule thereof, particularly di-2-methacryloxyethyl-2,2,4-trimethylhexamethylene dicarbamate and an acrylate corresponding thereto. These methacrylates or acrylates are known as a dental material and can be used singly or in admixture, if desired.

The (meth)acrylic ester monomer not having a benzene ring in a molecule thereof preferably has a refractive index, in terms a polymer thereof, equal to or less than that of the amorphous inorganic material having a refractive index in a D-line of sodium in the range of 1.470~1.520 and having an X-ray opacity. Usually, a monomer having a refractive index, in terms of a polymer thereof, in the range of 1.400~1.520, is used in an amount of about 75~25% by volume.

The above-described amorphous inorganic material and the polymer of the (meth)acrylic ester monomer not having a benzene ring in a molecule thereof are different from each other in wavelength reliance of the refractive index in a visible light region. That is, the refractive index of the polymer remarkably increases in a short wavelength side than 500 nm due to the constitutional elements and chemical structure thereof, as compared with the amorphous inorganic material. For this reason, a dental restorative material comprising the polymer as a matrix and the amorphous inorganic material as a filler relies on the wavelength with respect to the light transmittance and scattering in a visible light region. In case that the refractive index of the amorphous inorganic material is higher than that of the polymer over the whole of a visible light region, the difference in the refractive index is large in the long wavelength side, wherein the above-described opal-effect like optical characteristics are not exhibited, thereby obtaining a dental restorative material with a natural feeling. Also, in case that the refractive index in a D-line of sodium of the amorphous inorganic material is equal to that of the polymer, since a light scattering is slightly observed in both the long and short wavelength sides than the D-line of sodium, the above-described opal-effect like optical characteristics are not exhibited, thereby obtaining a dental restorative material with a natural feeling. For these reasons, when the refractive index in a D-line of sodium of the polymer of the (meth)acrylic ester monomer not having a benzene ring in a molecule thereof is equal to or less than the refractive index of the amorphous inorganic material having a refractive index in a D-line of sodium in the range of 1.470~1.520 and having an X-ray opacity, a dental restorative material having superior esthetics can be obtained.

On the other hand, in case that the refractive index of the amorphous inorganic material is lower than that of the polymer of the (meth)acrylic ester monomer not having a benzene ring in a molecule thereof over the whole of a visible light region, since the light scattering becomes strong in the short wavelength, the above-described opal-effect like optical characteristics are exhibited. Thus, in order to obtain a dental restorative material with a natural feeling, the volume fraction of the amorphous inorganic material must be restricted. Actually, since the refractive index of the polymer changes by the polymerization of the monomer, in case that the refractive index in a D-line of sodium is lower than that of the amorphous inorganic material before the polymerization, while it is higher than that of the amorphous inorganic material after the polymerization, the opal-effect like optical characteristics are exhibited only after the polymerization, the hue remarkably changes. For this reason, in case that the amorphous inorganic material having a refractive index of less than that of the polymer of the (meth)acrylic ester monomer not having a benzene ring in a molecule thereof is contained in combination, a suitable content thereof is from about 0.01~7% by volume. In this case, a dental restorative material having superior esthetics, whose opal-effect like optical characteristics are properly low, is obtained.

As the polymerization initiator which is used as a third major constitutional component is generally used a photopolymerization initiator comprising a combination of a sensitizing agent with a reducing agent. Examples of the sensitizer include camphorquinone, benzil, diacetyl, benzyl dimethyl ketal, benzyl diethyl ketal, benzyl di(2-methoxyethyl) ketal, 4,440-dimethyl benzyl-dimethyl ketal, anthraquinone, 1-chloroanthraquinone, 2-chloroanthraquinone, 1,2-benzanthraquinone, 1-hydroxyanthraquinone, 1-Methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-di-ethylthioxanthone, 2,4-diisopropylthioxanthone, 2-chloro-7-trifluoromethylthioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylaminophenyl) ketone, 4,440-bisdiethylaminobenzophenone, acyl phosphine oxides such as (2,4,6-trimethylbenzoyl)diphenylphosphine oxide, and azide containing compounds. These compounds can be used singly or in admixture.

As the reducing agent, tertiary amines are generally used. Suitable examples of tertiary amines include N,N-dimethylaminoethyl methacrylate, triethanolamine, N,N-dimethyl-p-toluidine, methyl 4-dimethylaminobenzoate, ethyl 4-dimethylaminobenzoate, and isoamyl 4-dimethylaminobenzoate. Other examples of the reducing agent include benzoyl peroxide, sodium sulfonate derivatives, and organometallic compounds.

In case that such a photopolymerization initiator is used, the polymerization reaction is achieved upon irradiation with actinic rays such as an ultraviolet light and a visible light. Examples of light sources which can be used include various mercury vapor pressure lamps including ultrahigh-pressure, high-pressure, medium-pressure, and low-pressure ones, a chemical lamp, a carbon arc lamp, a metal halide lamp, a fluorescent lamp, a tungsten lamp, a xenon lamp, and an argon ion laser.

Needless to say, as other polymerization initiators, known chemical polymerization initiators can be used which are represented by a combination of benzoyl peroxide with a tertiary amine or a combination of benzoyl peroxide with sodium benzene sulfonate.

Usually, these polymerization initiators can be used in an amount of about 0.001~3% by volume.

Needless to say that if desired, known additives which are usually used, such as ultraviolet light absorbers and polymerization inhibitors, can be properly compounded.

The present invention is hereunder specifically described with reference to the Examples, but it is not to be construed that the invention is limited to these Examples. The measurement of various characteristics, the preparation of various amorphous inorganic material, and the preparation of dental restorative materials were carried out in the following manners.

EXAMPLES

X-Ray Opacity

The test was carried out according to ISO 4049–1988. That is, relative photographing was carried out by using aluminum plates having a thickness of 0.5~5.0 mm (0.5 mm step), the resulting images were read by means of a densitometer (a trade name "PDA-81, made by Konica Corporation), a calibration curve was obtained from the values of the aluminum plates, and an aluminum thickness corresponding to 1 mm of the specimen was calculated from the calibration curve.

Measurement of Mean Particle Size

In a dry 50-ml beaker was charged by three microspatulas of a uniformly mixed sample powder. After adding 30 ml of a dispersion medium (a 0.3 wt % sodium hexametaphosphate aqueous solution) thereto, the mixture was stirred and irradiated with an ultrasonic wave for 3 minutes to prepare a slurry solution. By using this slurry, the measurement was carried out by means of laser diffraction type particle size distribution device (a trade name "SALD-1000", made by Shimadzu Corporation).

Refractive Index

A refractive index in a D-line of powder sodium was measured in the following manner. That is, a sample powder was charged in a test tube; a mixed solution of xylene, heptane and chloronaphthalene having a refractive index lower than an expected refractive index was added thereto; and a mixed solution of xylene, heptane and chloronaphthalene having a refractive index higher than an expected refractive index was properly added thereto. After mixing, the resulting mixture was observed in a D-line of sodium. A mixed solution having a ratio when the refractive index of the mixed solution became identified with that of the sample powder, whereby the sample powder had substantially disappeared, was again prepared. Further, several kinds of mixed solutions having a different refractive index in a D-line of sodium from each other by about 0.002 were prepared and independently added in a test tube having the sample powder charged therein, followed by making comparison. Of these mixed solutions, the mixed solution imparting a highest transparency was measured in terms of refractive index by means of an Abbe-refractometer, and the resulting refractive index was defined to be a refractive index of the sample powder. The measurement was carried out at 23° C. and at 50% RH (relative humidity).

A refractive index in a D-line of sodium of the polymer was carried out in the following manner. That is, a predetermined compounding amount of a monomer having 0.5 part by weight of azobisisobutyronitrle added thereto was poured into a glass frame and heated for curing to obtain a plate. A refractive index of the plate was measured by using chloronaphthalene as an intermediate solution by means of an Abbe-refractometer. The measurement was carried out at 23° C. and at 50% RH (relative humidity).

Transparency and Colorimetry of Polymerized Dental Restorative Material

A dental restorative material to be tested was filled in a mold having an inside diameter of 20 mm and a thickness of 1 mm and brought into press contact with a glass sheet via cellophane, followed by irradiation with a light for 5 minutes by means of a visible light exposure (a trade name "GC Labo Light LV-II", made by GC Corporation). After polishing out with an emery paper #600, the resulting assembly was polished successively with a water paste of dental polishing sand (fine) and a water paste of finish polishing alumina (0.3 µm), thereby finishing it so as to have a thickness of (1.00±0.01)mm. The light irradiation was carried out from 1 m in the sample surface direction by using a colorimetry light source (a trade name "Sun Ream", made by Daiwa Lighting Corporation) as a light source. The colorimetry was carried out by using a photo diode array type spectrophotometer (a trade name "Spectra Scan PR650", made by Photo Research Corporation), and a central portion of 3 mm in diameter of the sample surface on a light trap or a standard white board (magnesium oxide) was measured at an angle of 45° against the sample surface direction.

The translucency was evaluated by calculating $L^*$(black) and $L^*$(white) in a CIE-$L^*a^*b^*$ color specification system and defining a value represented by the following equation:

$$[L^*(white)-L^*(black)]/L^*(white)$$

as an index. Also, the color of the cured product was evaluated by $a^*$ and $b^*$ in a CIE-$L^*a^*b^*$ color specification system. That is, when the polymerized material is observed to have opal-effect like optical characteristics, the hue on the standard white board (magnesium oxide) is reddish, while the hue on the light trap is bluish.

The results are summarized in Table 3.

Preparation of Amorphous Inorganic Material Having X-ray Opacity

According to the description of Japanese Patent Publication No. 7-55882(1995), predetermined amounts of kaolin, strontium carbonate, aluminum phosphate, aluminum fluoride, and quartz were compounded and thoroughly mixed with each other; the mixture was melted at 1,400° C. for 3 hours in an alumina crucible; and the melt was quenched by sandwiching by metal rolls rotating at a high speed to form a glass. The resulting glass powder was further pulverized to prepare a glass powder having a maximum particle size of 3 µm and a mean particle size of 0.8 µm. Also, in Example 5, the pulverization time was changed to prepare a glass powder having a maximum particle size of 45 µm and a mean particle size of 11 µm. The conversion amounts of the amorphous inorganic materials used in Examples 1 to 6 and Comparative Examples 1 and 6 are shown in Tables 1 and 2, respectively. [Preparation of amorphous inorganic material having a refractive index equal to or less than that of a polymer of a monomer]

An amorphous inorganic material having a refractive index equal to or less than that of a polymer of a monomer was prepared in the following manner. That is, predetermined amounts of potassium carbonate and quartz were compounded in potassium feldspar ($K_2O.Al_2O_3.6SiO_2$), and the mixture was melted at 1,550° C. for 3 hours in an alumina crucible. The resulting crucible was thrown into water to form a glass. The resulting glass was taken out from the crucible and further pulverized to prepare glass powders having a maximum particle size of 2 µm and a mean particle size of 0.7 µm for Examples 1 to 4 and 6 and Comparative Examples 1 and 2. Also, in Example 5, the pulverization time was changed to prepare a glass powder having a maximum particle size of 45 µm and a mean particle size of 11 µm. Incidentally, in Example 3, commercially available amorphous silica (a trade name "Adma Fine SO-C2", made by Admatex Corporation) was used. The conversion amounts of the amorphous inorganic materials used in Examples 1 to 6 and Comparative Examples 1 and 2 are shown in Tables 1 and 2, respectively.

Preparation of Dental Restorative Material

The compounding amounts of the dental restorative materials in the respective Examples and Comparative Examples are shown in Tables 1 and 2. Incidentally, all of the amorphous inorganic materials having an X-ray opacity and the amorphous inorganic materials having a refractive index equal to or less than that of a polymer of a monomer were used after modifying with 2 parts by weight of 3-methacryloxypropyl trimethoxysilane.

TABLE 1

| Example | Amorphous inorganic material having X-ray opacity | Amorphous inorganic material having a refractive index equal to or less than that of a polymer of a monomer | (Meth)acrylic ester monomer | Polymerization initiator |
|---|---|---|---|---|
| 1 | 72% by volume | — | 27.8% by volume | 0.04% by volume |
|   | $SiO_2$ 24% by weight<br>$Al_2O_3$ 20% by weight<br>$P_2O_5$ 2% by weight<br>SrO 38% by weight<br>$F_2$ 16% by weight<br>Refractive index: nD = 1.518 | | Urethane dimethacrylate 80% by weight<br>Triethylene glycol dimethacrylate 20% by weight<br>Refractive index: nD = 1.509 | Camphorquinone 0.16% by volume<br>N,N-Dimethylaminoethyl-methacrylate |
| 2 | 60.3% by volume | 7% by volume | 32.5% by volume | 0.04% by volume |
|   | $SiO_2$ 32% by weight<br>$Al_2O_3$ 31% by weight<br>$P_2O_5$ 2% by weight<br>SrO 31% by weight<br>$F_2$ 4% by weight<br>Refractive index: nD = 1.509 | $SiO_2$ 65% by weight<br>$Al_2O_3$ 15% by weight<br>$K_2O$ 20% by weight<br>Refractive index: nD = 1.488 | Urethane trimethacrylate 20% by weight<br>Urethane dimethacrylate 30% by weight<br>Neopentyl glycol dimethacrylate 30% by weight<br>2-Hydroxy-1,3-dimethacryoxy propane 20% by weight<br>Refractive index: nD = 1.489 | Camphorquinone 0.16% by volume<br>N,N-Dimethyl-p-toluidine |
| 3 | 65% by volume | 3% by volume | 31.8% by volume | 0.04% by volume |
|   | $SiO_2$ 41% by weight<br>$Al_2O_3$ 20% by weight<br>$P_2O_5$ 3% by weight<br>SrO 16% by weight<br>$F_2$ 20% by weight<br>Refractive index: nD = 1.474 | $SiO_2$ 100% by weight<br>Refractive index: nD = 1.442 | Urethane diacrylate 70% by weight<br>Neopentyl glycol dimethacrylate 30% by weight<br>Refractive index: nD = 1.473 | Benzyl dimethyl ketal 0.16% by volume<br>N,N-Dimethyl-p-toluidine |
| 4 | 28.5% by volume | 6% by volume | 65.3% by volume | 0.04% by volume |
|   | $SiO_2$ 47% by weight<br>$Al_2O_3$ 20% by weight<br>$P_2O_5$ 0% by weight<br>SrO 19% by weight<br>$F_2$ 14% by weight<br>Refractive index: nD = 1.510 | $SiO_2$ 88% by weight<br>$Al_2O_3$ 5% by weight<br>$K_2O$ 7% by weight<br>Refractive index: nD = 1.471 | Urethane dimethacrylate 80% by weight<br>Triethylene glycol dimethacrylate 20% by weight<br>Refractive index: nD = 1.509 | Camphorquinone 0.16% by volume<br>N,N-Dimethylaminoethyl-methacrylate |
| 5 | 41% by volume | 7% by volume | 51.8% by volume | 0.04% by volume |
|   | $SiO_2$ 24% by weight<br>$Al_2O_3$ 20% by weight<br>$P_2O_5$ 2% by weight<br>SrO 38% by weight<br>$F_2$ 16% by weight<br>Refractive index: nD = 1.518 | $SiO_2$ 65% by weight<br>$Al_2O_3$ 15% by weight<br>$K_2O$ 20% by weight<br>Refractive index: nD = 1.488 | Urethane dimethacrylate 80% by weight<br>Triethylene glycol dimethacrylate 20% by weight<br>Refractive index: nD = 1.509 | Benzyl dimethyl ketal 0.16% by volume<br>N,N-Dimethylaminoethyl-methacrylate |
| 6 | 25.8% by volume | 1% by volume | 73% by volume | 0.04% by volume |
|   | $SiO_2$ 32% by weight<br>$Al_2O_3$ 31% by weight<br>$P_2O_5$ 2% by weight<br>SrO 31% by weight<br>$F_2$ 4% by weight<br>Refractive index: nD = 1.509 | $SiO_2$ 41% by weight<br>$Al_2O_3$ 20% by weight<br>$P_2O_5$ 3% by weight<br>SrO 16% by weight<br>$F_2$ 20% by weight<br>Refractive index: nD = 1.474 | Urethane trimethacrylate 20% by weight<br>Urethane dimethacrylate 30% by weight<br>Neopentyl glycol dimethacrylate 30% by weight<br>2-Hydroxy-1,3-dimethacryoxy propane 20% by weight<br>Refractive index: nD = 1.489 | Camphorquinonel 0.16% by volume<br>N,N-Dimethyl-p-toluidine |

TABLE 2

| Comparative Example | Amorphous inorganic material having X-ray opacity | Amorphous inorganic material having a refractive index equal to or less than that of a polymer of a monomer | (Meth)acryic ester monomer | | Polymerization initiator |
|---|---|---|---|---|---|
| 1 | 75% by volume | — | 24.3% by volume | | 0.04% by volume |
| | SiO$_2$ 24% by weight | | Bisphenol A glydidyl | 75% by weight | Camphorquinone |
| | Al$_2$O$_3$ 20% by weight | | methacrylate | | 0.16% by volume |
| | P$_3$O$_5$ 2% by weight | | Triethylene glycol | 25% by weight | N,N Dimethyl- |
| | SrO 38% by weight | | dimethacrylate | | aminoethyl- |
| | F$_2$ 16% by weight | | Referactive index: nD = 1.549 | | methacrylate |
| | Refractive index: nD = 1.518 | | | | |
| 2 | 25% by volume | 8% by volume | 66.8% by volume | | 0.04% by volume |
| | SiO$_2$ 32% by weight | SiO$_2$ 88% by weight | Urethane trimethacrylate | 20% by weight | Camphorquinone |
| | Al$_2$O$_3$ 31% by weight | Al$_2$O$_3$ 5% by weight | Urethane dimethacrylate | 30% by weight | 0.16% by volume |
| | P$_3$O$_5$ 2% by weight | K$_2$O 7% by weight | Neopentyl glycol | 30% by weight | N,N Dimethyl-p- |
| | SrO 31% by weight | Refractive index: nD = 1.471 | dimethacrylate | | toluidine |
| | F$_2$ 4% by weight | | 2-Hydroxy-1,3-dimetha- | 20% by weight | |
| | Refractive index: nD = 1.535 | | cryoxy propane | | |
| | | | Referactive index: nD = 1.489 | | |

TABLE 3

| | On standard white board | | | On light trap | | | Translucency | X-Ray capacity [Thickness (mm) corresponding to 1-mm aluminum] | Characteristics |
|---|---|---|---|---|---|---|---|---|---|
| | L* | a* | b* | L* | a* | b* | | | |
| Example 1 | 96.6 | 0.3 | 6.2 | 34.6 | 0.4 | 3.2 | 0.64 | 2.71 | No change in hue by the thickness occurred. |
| Example 2 | 95.6 | 1.1 | 5.5 | 63.0 | 1.9 | 1.1 | 0.34 | 2.56 | No change in hue by the thickness occurred. A proper opal-effect was observed. |
| Example 3 | 92.1 | 2.2 | 8.9 | 49.9 | 3.2 | 4.4 | 0.46 | 1.99 | No change in hue by the thickness occurred. A proper opal-effect was observed. |
| Example 4 | 94.5 | 1.2 | 5.8 | 53.9 | 2.2 | 3.7 | 0.43 | 2.31 | No change in hue by the thickness occurred. A proper opal-effect was observed. |
| Example 5 | 97.2 | 0.9 | 8.6 | 64.9 | 1.8 | 4.4 | 0.33 | 2.59 | No change in hue by the thickness occurred. A proper opal-effect was observed. |
| Example 6 | 94.9 | 2.8 | 7.1 | 48.5 | 3.3 | 2.0 | 0.49 | 2.70 | No change in hue by the thickness occurred. A proper opal-effect was observed. |
| Comparative Example 1 | 95.1 | 4.2 | 3.4 | 54.4 | 0.2 | -2.5 | 0.43 | 2.70 | The opal-effect was observed too much. |
| Comparative Example 2 | 97.2 | 2.9 | 4.6 | 72.1 | 0.4 | -1.1 | 0.26 | 2.60 | The opal-effect was observed too much. Opaque |

As described above in detail, the dental restorative material according to the present invention is free from a fear of the action by an environmental hormone by the use of a monomer matrix system not having a benzene ring. Also, by the combination of a monomer with an amorphous inorganic material having a proper refractive index, the dental restorative material according to the present invention realizes translucency close to natural teeth, has an X-ray opacity, and has superior esthetics such that the hue does not rely on the thickness. Thus, dental restorative material according to the present invention can be widely used and greatly contribute to the field of dental remedy.

While the invention has been described in detail and with reference to specific embodiments thereof, it will be apparent to one skilled in the art that various changes and modifications can be made therein without departing from the spirit and scope thereof.

What is claimed is:

1. A dental restorative material consisting of:
   an amorphous inorganic material having a refractive index in a D-line of sodium in the range of 1.470~1.520 and having an X-ray opacity;
   at least one (meth)acrylic ester monomer not having a benzene ring in a molecule thereof; and
   at least one polymerization initiator,
   wherein said amorphous inorganic material contains Si, Al, P, Sr, F, and O in conversion amounts from 20 to 50% by weight for SiO$_2$, from 20 to 40% by weight for Al$_2$O$_3$, from 0 to 15% by weight for P$_2$O$_5$, from 15 to 40% by weight for SrO, and from 3 to 20% by weight for F$_2$, respectively, and is substantially free from alkali metal elements and from Be, Mg and Ba; and
   wherein a polymer of said (meth) acrylic ester monomer not having a benzene ring in a molecule thereof has a refractive index in a D-line of sodium equal to or less than a refractive index in a D-line of sodium of said amorphous inorganic material.

2. The dental restorative material according to claim 1, further comprising
   an amorphous inorganic material having a refractive index in a D-line of sodium equal to or less than the refractive index in a D-line of sodium of a polymer of said (meth)acrylic ester monomer not having a benzene ring in a molecule thereof.

3. The dental restorative material according to claim 2, wherein
said amorphous inorganic material having a refractive index in a D-line of sodium in the range of 1.470~1.520 and having an X-ray opacity and/or
said amorphous inorganic material having a refractive index in a D-line of sodium equal to or less than the refractive index in a D-line of sodium of a polymer of said (meth)acrylic ester monomer not having a benzene ring in a molecule thereof
are/is modified on its surface with a silane coupling agent having an unsaturated double bond.

4. The dental restorative material according to claim 2, wherein
said amorphous inorganic material having a refractive index in a D-line of sodium in the range of 1.470~1.520 and having an X-ray opacity and/or
said amorphous inorganic material having a refractive index in a D-line of sodium equal to or less than the refractive index in a D-line of sodium of a polymer of said (meth)acrylic ester monomer not having a benzene ring in a molecule thereof
has a mean particle size of from 0.01 to 50 $\mu$m.

5. The dental restorative material according to claim 2, wherein
said amorphous inorganic material having a refractive index in a D-line of sodium in the range of 1.470~1.520 and having an X-ray opacity and/or
said amorphous inorganic material having a refractive index in a D-line of sodium equal to or less than the refractive index in a D-line of sodium of a polymer of said (meth)acrylic ester monomer not having a benzene ring in a molecule thereof
has a maximum particle size of 0.05~7 $\mu$m and a mean particle size of 0.01~2.0 $\mu$m.

6. The dental restorative material of claim 1, wherein said amorphous inorganic material is modified on its surface with a silane coupling agent having an unsaturated double bond.

7. The dental restorative material of claim 1, wherein said amorphous inorganic material has a mean particle size of from 0.01 to 50 $\mu$m.

8. The dental restorative material of claim 1, wherein said amorphous inorganic material has a maximum particle size of 0.05~7 $\mu$m and a mean particle size of 0.01~2.0 $\mu$m.

9. A dental restorative material consisting of:
an amorphous inorganic material having a refractive index in a D-line of sodium in the range of 1.470~1.520 and having an X-ray opacity;
at least one (meth)acrylic ester monomer not having a benzene ring in a molecule thereof; and
at least one polymerization initiator,
wherein said amorphous inorganic material contains Si, Al, P, Sr, F, and O in conversion amounts from 20 to 50% by weight for $SiO_2$, from 20 to 40% by weight for $Al_2O_3$, from 0 to 15% by weight for $P_2O_5$, from 15 to 40% by weight for SrO, and from 3 to 20% by weight for $F_2$, respectively, and is substantially free from alkali metal elements and from Be, Mg and Ba; and
wherein a polymer of said (meth) acrylic ester monomer not having a benzene ring in a molecule thereof has a refractive index in a D-line of sodium equal to or less than a refractive index in a D-line of sodium of said amorphous inorganic material; and wherein said dental restorative material is a dental resin or resin cement.

10. The material of claim 1, wherein said inorganic material has an X-ray opacity ranging from 1.99 to 2.71 as determined according to ISO 4049–1988.

* * * * *